United States Patent [19]

Combs et al.

[11] Patent Number: 5,030,635

[45] Date of Patent: Jul. 9, 1991

[54] 6-7-DIMETHOXY-1,2-DIHYDRO-2-ARYL-QUINAZOLINE-3-OXIDES

[75] Inventors: Donald W. Combs, Piscataway; Robert Falotico, Belle Mead; David M. Ritchie, Princeton Junction, all of N.J.

[73] Assignee: Ortho Pharmaceutical Corporation, Raritan, N.J.

[21] Appl. No.: 564,906

[22] Filed: Aug. 8, 1990

Related U.S. Application Data

[62] Division of Ser. No. 479,796, Feb. 14, 1990, Pat. No. 4,963,554.

[51] Int. Cl.$^5$ .................. A61K 31/505; C07D 403/04
[52] U.S. Cl. .................................. 514/259; 544/283; 544/284
[58] Field of Search .......................................... 514/259

[56] References Cited

U.S. PATENT DOCUMENTS

| | | | |
|---|---|---|---|
| 3,476,756 | 11/1969 | Taylor et al. | 544/283 |
| 4,343,940 | 8/1982 | Kreighbaum et al. | 544/283 |
| 4,745,118 | 5/1988 | Combs et al. | 544/283 |

Primary Examiner—C. Warren Ivy
Assistant Examiner—James H. Turnipseed
Attorney, Agent, or Firm—Benjamin F. Lambert

[57] ABSTRACT

Novel 6,7-dimethoxy-1,2-dihydro-2-arylquinazoline-3-oxides and their synthesis are described. These novel compounds are cardiotonic agents and bronchodilating agents, and as such are useful for the treatment of heart failure and asthma.

4 Claims, No Drawings

6-7-DIMETHOXY-1,2-DIHYDRO-2-ARYL-QUINAZOLINE-3-OXIDES

This is a division of application Ser. No. 479,796, filed Feb. 14, 1990, now U.S. Pat. No. 4,963,554.

BACKGROUND OF THE INVENTION

1. Field of the Invention

The present invention relates to novel 6,7-dimethoxy-1,2-dihydro-2-arylquinazoline-3-oxides of the formula

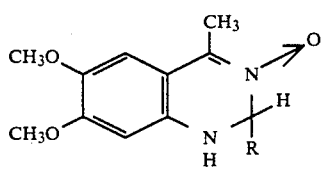

as described further below. These compounds are useful as cardiotonic agents and bronchodilators.

2. Description of the Prior Art

No examples of 6,7-dimethoxy substituted 2-arylquinazoline-3-oxides have been seen in the prior art. However, other compounds of this structural class have been previously described.

Fey et al., *J. Prakt. Chem.* 5-6, 225-235 (1967) described 2-arylquinazoline-3-oxides of the formula

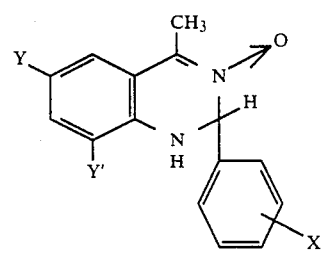

where
X is hydrogen, 4-acetylamino, 4-dimethylamino, 2-nitro, 4-nitro or 4-methoxy; and
Y and Y' are the same or different and are hydrogen or bromo.

Also described in the Fey et al. reference is a compound of the formula

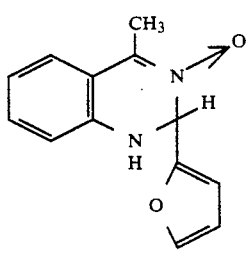

*Chemical Abstract* 62, 16241/E; Kovendi et al., *Chem. Ber.* 98, 1049 (1965) also describes 2-arylquinazoline-3-oxides of the formula

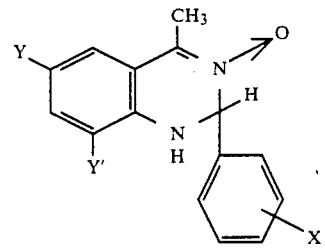

where
X is hydrogen, 4-acetylamino,4-dimethylamino,2-nitro, 3-nitro,4-nitro, 3,4-dimethoxy,2-hydroxy, or 4-methoxy; and
Y and Y' are the same or different and are hydrogen or bromo.

Like Fey et al., the *Chemical Abstract* also describes another 2-arylquinazoline-3-oxide of the formula

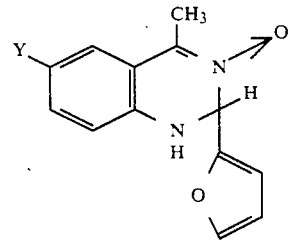

where
Y is hydrogen or bromo.

Atmaram et al., *Acta Chem. Scand. Ser. B* B36, 641 (1982), further describes a 2-arylquinazoline-3-oxide of the formula

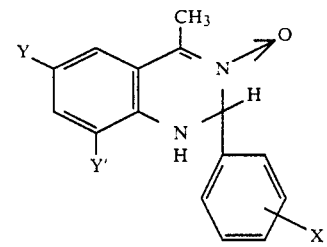

where
X, Y and Y' are hydrogen.

SUMMARY OF THE INVENTION

The present invention is directed to 6,7-dimethoxy-1,2-dihydro-2-arylquinazoline-3-oxides of the formula

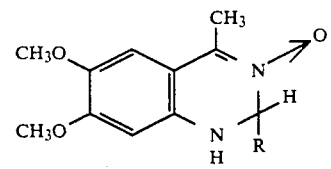

where
R may be phenyl, substituted phenyl or heteroaryl; wherein the substituted phenyl may be substituted with halogen, $C_1$-$C_6$ alkyl, $C_1$-$C_6$ alkoxy, methylenedioxy, nitro, benzyloxy, amino or substituted amino, and the heteroaryl may be furyl, thienyl, pyrrolo, N-substituted pyrrolo, pyridyl or substituted heteroaryl; wherein the substituted amino may be substituted with $C_1$-$C_6$ alkyl or $C_1$-$C_6$ dialkyl, the N-substituted pyrrolo may be substituted with $C_1$-$C_6$ alkyl and the substituted heteroaryl may be substituted with halogen, $C_1$-$C_6$ alkyl, $C_1$-$C_6$ alkoxy, methylenedioxy, nitro, benzyloxy, amino or substituted amino; wherein the substituted amino may be substituted with $C_1$-$C_6$ alkyl or $C_1$-$C_6$ dialkyl.

The compounds of the present invention are cardiotonic agents and bronchodilators, useful for the treatment of heart failure and asthma in mammals.

DETAILED DESCRIPTION OF THE INVENTION

The invention in its broadest aspects relates to 6,7-dimethoxy-1,2-dihydro-2-arylquinazoline-3-oxides which have cardiotonic activity or bronchodilating activity in mammals. The 6,7-dimethoxy-1,2-dihydro-2-arylquinazoline-3-oxides of the invention have the formula

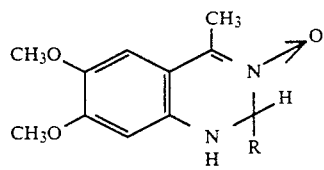

where R is as defined above.

The preferred compounds of the present invention are those wherein R is phenyl, substituted phenyl, furyl, thienyl, pyrrolo, N-substituted pyrrolo or pyridyl.

The compounds of the present invention can be prepared as shown in the following scheme.

SCHEME

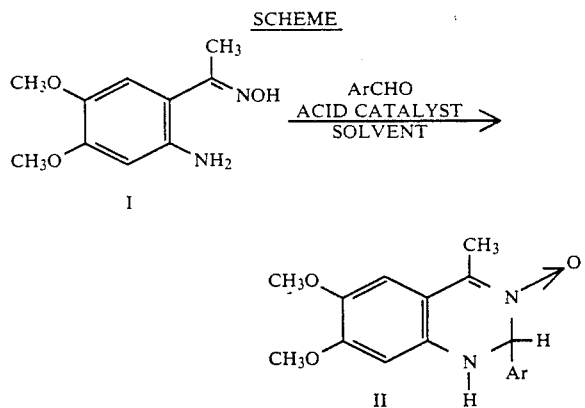

The 6,7-dimethoxy-1,2-dihydro-2-arylquinazoline-3-oxides (II) are prepared from the oxime (I). The oxime (I) is prepared using the techniques described by Simpson, *J. Chem. Soc.* 94 (1946).

The oxime (I) is suspended or dissolved in a solvent such as toluene, benzene, or an alcohol such as methanol or ethanol. To the suspension or solution is added an appropriate aromatic aldehyde (ArCHO) and a catalytic amount of a mineral acid such as sulfuric acid or hydrochloric acid or an organic acid such as p-toluenesulfonic acid. The mixture is stirred at temperatures ranging from room temperature to reflux, and the product is then collected by filtration as an insoluble precipitate after 15 minutes to two hours (Kovendi et al., *Chem. Ber.* 98, 11049 (1965)).

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage forms, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions) or carriers such as starches, sugars, diluents, granulating agents, lubricants, binders, disintegrating agents and the like in the case of oral solid preparations (such as, for example, powders, capsules and tablets). Because of their ease of administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.5 to about 100 mg/kg, and preferably about about 1 to about 5 mg/kg of the active ingredient.

The following examples described the invention in greater particularity and are intended to illustrate but not limit the invention.

EXAMPLE 1

1,2-Dihydro-2-phenyl-4-methyl-6,7-dimethoxy-quinazoline-3-oxide

2-Amino-4,5-dimethoxyacetophenone oxime (2.0 g, 9.5 mmol) was suspended in 80 ml benzene, and 1.01 g of benzaldehyde was added followed by a spatula-full of p-toluenesulfonic acid. After 1 hour the mixture was poured into hexane and the yellow solid was collected by filtration, and washed with ethyl acetate to yield 1.0 g (67%) of the title compound. m.p. 178°–182° C.

| | C, | H, | N, |
|---|---|---|---|
| Calc for $C_{17}H_{18}N_2O_3$: | C, 68.43; | H, 6.09; | N, 9.39. |
| Found: | C, 68.08; | H, 6.13; | N, 9.07. |

When in the above procedure, 2-nitrobenzaldehyde is used instead of benzaldehyde, then 1,2-dihydro-2-(2-nitrophenyl)-4-methyl-6,7-dimethoxyquinazoline-3-oxide is obtained.

EXAMPLE 2

1,2-Dihydro-2-(4-chlorophenyl)-4-methyl-6,7-dimethoxyquinazoline-3-oxide

The title compound was synthesized using the procedures of Example 1 with toluene as the solvent and p-chlorobenzaldehyde as the aldehyde. Chromatography on silica gel using methylene chloride-methanol as the eluent gave, after recrystallization from ethyl acetate-hexane, a 19% yield of product, mp 90°–93° C.

| Calc for $C_{17}H_{17}ClN_2O_3$: | C, 61.35; | H, 5.16; | N, 8.42. |
| Found: | C, 61.34; | H, 5.07; | N, 8.28. |

When in the above procedure, 3-nitrobenzaldehyde is used as the aldehyde, then 1,2-dihydro-2-(3-nitrophenyl)-4-methyl-6,7-dimethoxyquinazoline-3-oxide is obtained.

EXAMPLE 3

1,2-Dyhydro-2-(4-methoxyphenyl)-4-methyl-6,7-dimethoxyquinazoline-3-oxide

The title compound was synthesized using the procedures of Example 1 with anisaldehyde as the aldehyde. Chromatography on silica gel using methylene chloride-methanol as eluent gave, after recrystallization from ethyl acetate-ether, the product in 15% yield. m.p. 161°–163° C.

| Calc for $C_{18}H_{20}N_2O_4$: | C, 65.83; | H, 6.15; | N, 8.53. |
| Found: | C, 65.43; | H, 6.27; | N, 8.60. |

When in the above procedure, 4-nitrobenzaldehyde is used as the aldehyde, then 1,2-dihydro-2-(4-nitrophenyl)-4-methyl-6,7-dimethoxyquinazoline-3-oxide is obtained.

EXAMPLE 4

1,2-Dihydro-2-(4-tolyl)-4-methyl-6,7-dimethoxyquinazoline-3-oxide

The title compound was synthesized using the procedures of Example 1 with p-tolualdehyde as the aldehyde. Chromatography on silica gel using methylene chloride-methanol as eluent gave, after recrystallization from ethyl acetate-ether, a 37% yield of the product. m.p. 155°–158° C.

| Calc for $C_{18}H_{20}N_2O_3$: | C, 69.20: | M, 6.47; | N, 8.97. |
| Found: | C, 68.99; | H, 6.53; | N, 8.87. |

When in the above procedure, 2-aminobenzaldehyde is used as the aldehyde, then 1,2-dihydro-2-(2-aminophenyl)-4-methyl-6,7-dimethoxyquinazoline-3-oxide is obtained.

EXAMPLE 5

1,2-Dihydro-2-(3,4-methylenedioxyphenyl)-4-methyl-6,7-dimethoxyquinazoline-3-oxide The title compound was synthesized using the procedures of Example 1 with piperonal instead of benzaldehyde as the aldehyde. The solvent was dissolved in methylene chloride and filtered through a silica gel plug, evaporated, and then recrystallized from methanolethyl acetate to give a 20% yield of the product. m.p. 186°–189° C.

| Calc for $C_{18}H_{18}N_2O_5$: | C, 63.14; | H, 5.31; | N, 8.18. |
| Found: | C, 63.22; | H, 5.23; | N, 7.78. |

EXAMPLE 6

1,2-Dihydro-2-(2,3-methylenedioxyphenyl)-4-methyl-6,7-dimethoxyquinazoline-3-oxide The title compound was synthesized using the procedures of Example 1 with 2,3-methylene dioxybenzaldehyde as the aldehyde. The solid was recrystallized from ethyl acetate-methanol to give a 8.6% yield of the product. m.p. 185°–189° C.

| Calc for $C_{18}H_{18}N_2O_5$: | C, 63.14; | H, 5.31; | N, 8.18 |
| Found: | C, 62.85; | H, 5.31; | N, 7.81. |

EXAMPLE 7

1,2-Dihydro-2-(3-benzyloxyphenyl)-4-methyl-6,7-dimethoxyquinazoline-3-oxide

The title compound was synthesized using the procedures of Example 1 with toluene as the solvent and 3-benzyloxybenzaldehyde as the aldehyde. Washing of the resulting solid with ether gave a 95% yield of the product. m.p. 170°–172° C.

| Calc for $C_{24}H_{24}N_2O_4$: | C, 71.26; | H, 5.99; | N, 6.93. |
| Found: | C, 70.77; | H, 6.12; | N, 6.77. |

EXAMPLE 8

1,2-Dihydro-2-pentafluorophenyl-4-methyl-6,7-dimethoxyquinazoline-3-oxide

The title compound was synthesized using the procedures of Example 1 with toluene as the solvent and pentafluorobenzaldehyde as the aldehyde. The product was washed with hexane to yield the title compound (99%). m.p. 177.5°–179.5° C.

| Calc for $C_{17}H_{13}F_5N_2O_3$: | C, 52.28; | H, 3.83; | N, 7.22. |
| Found: | C, 52.79; | H, 3.50; | N, 7.09. |

EXAMPLE 9

1,2-Dihydro-2-(2-furyl)-4-methyl-6,7-dimethoxyquinazoline-3-oxide

The title compound was synthesized using the procedures of Example 1 with 2-furaldehyde as the aldehyde. The product was recrystallized from methanol-ether giving a 16% yield. m.p. 191°–195° C.

| Calc for $C_{15}H_{16}N_2O_4$: | C, 62.48; | H, 5.60; | N, 9.72. |
| Found: | C, 62.56; | H, 5.51; | N, 9.48. |

EXAMPLE 10

1,2-Dihydro-2-(2-thienyl)-4-methyl-6,7-dimethoxyquinazoline-3-oxide

The title compound was synthesized using the procedures of Example 1 with 2-thiophene carboxyaldehyde as the aldehyde. Recrystallization of the product from methanol-ether resulted in a 24% yield. m.p. 180°–185° C.

| Calc for $C_{15}H_{16}N_2O_3S$: | C, 59.20; | H, 5.31; | N, 9.21. |

| Found: | C, 59.21; | H, 5.22; | N, 9.08. |

EXAMPLE 11

1,2-Dihydro-2-(2-(N-methyl)pyrrolo)-4-methyl-6,7-dimethoxyquinazoline-3-oxide

The title compound was synthesized using the procedures of Example 1 with toluene as the solvent and N-methylpyrrole-2-carboxaldehyde as the aldehyde. The resultant solid was collected and washed with ethanol-ethyl acetate-ether to give a 58% yield of product with m.p. 179°–184° C.

| Calc for $C_{16}H_{19}N_2O_3$: | C, 63.76; | H, 6.37; | N, 13.95. |
| Found: | C, 63.62; | H, 6.60; | N, 13.83. |

EXAMPLE 12

1,2-Dihydro-2-(2-pyridyl)-4-methyl-6,7-dimethoxyquinazoline-3-oxide

The title compound was synthesized by the method of Example 1 using 2-pyridine carboxaldehyde as the aldehyde and recrystallizing from ethyl acetate-methanol to give a 75% yield of the product. m.p. 187°–189° C.

| Calc for $C_{16}H_{27}N_3O_3$: | C, 64.19; | H, 5.74; | N, 14.04. |
| Found: | C, 64.19; | H, 5.86; | N, 13.88. |

EXAMPLE 13

1,2-Dihydro-2-(4-pyridyl)-4-methyl-6,7-dimethoxyquinazoline-3-oxide

The title compound was synthesized by the method of Example 1 using 4-pyridine carboxaldehyde as the aldehyde and recrystallizing from ethyl acetate-methanol to give a 47% yield of the product. m.p. 179°–182° C.

| Calc for $C_{16}H_{17}N_3O_3$: | C, 64.19; | H, 5.74; | N, 14.04. |
| Found: | C, 63.74; | H, 5.64; | N, 13.79. |

EXAMPLE 14

Pharmacological Activity—Active Lung Anaphylaxis

Using the procedures described by Ritchie, D. M. et al., *Agents and Actions* 11, 4 (1981), male Harley guinea pigs were actively sensitized, intraperitoneally, with 16 mg alum and 1 mg ovalbumin. Fourteen days later, these animals were anesthetized and their respiration arrested by the administration of succinylcholine. Respiration was maintained at a constant pressure by a miniature Starling pump. Lung overflow changes in pressure were recorded.

Animals were pretreated with indomethacin (10 mg/kg, i.v.), atropine (0.5 mg/kg, i.v.), methysergide (0.1 mg/kg, i.v.), methapyrilene (2.0 mg/kg, i.v.) and arachidonic acid (5.0 mg/kg, i.v.) prior to ovalbumin challenge. The Example compounds (1.87 mg/kg or 8.75 mg/kg) were then administered by various routes prior to ovalbumin provocation. Indications of drug efficacy were manifested as a substantial reduction in the degree of bronchoconstriction evidenced by control animals.

Bronchoconstriction induced by ovalbumin was measured as a percent of maximum bronchoconstriction (BC) obtained by clamping off the trachea. Percent inhibition of control was determined as follows:

$$\% \text{ Inhibition of Control} = \frac{\text{Control \%Max } BC - \text{Treated \% Max } BC}{\text{Control \% Max } BC} \times 100$$

The results of this procedure are set forth below in Table 1.

EXAMPLE 15

Pharmacological Activity—Acute In Vivo Cardiotonic Evaluation

Using the procedures described by Alousi, A. A. et al., *Circ. Res.* 45, 666 (1979), adult mongrel dogs were anesthetized with sodium pentobarbital, and artificially respirated. Arterial pressure was recorded via a femoral artery and the pressure pulse was used to trigger a cardiotachometer for heart rate. Left ventricular pressure was measured with a Millar catheter, and dP/dt was derived. Cardiac output was determined by measuring ascending aortic blood flow with an electromagnetic flow probe, and the myocardial contractile force (CF) was measured with a Walton Brodie strain gauge sutured to the right ventricle. Lead II EKG was also recorded.

A standard dose of dopamine or dobutamine was administered in order to assess myocardial responsiveness. The test compounds were then administered by i.v. infusion and the effects on cardiovascular parameters were determined. The dose of each example compound was either 1.87 mg/kg or 8.75 mg/kg as set forth below in Table 1.

The dose related effects of the compound on myocardial contractile force was compared to pretreatment control values, expressed as a % change and rated for activity. Statistical evaluations were made using the appropriate parametric test against a vehicle control.

The results of the procedure are shown below in Table 1.

TABLE 1

| Example | % Increase In Myocardial Contractile force | % Inhibition of Bronchoconstriction at 50 mpk |
| --- | --- | --- |
| 1 | 157 at 8.75 mpk | 60.9 |
| 2 | 50 at 8.75 mpk | |
| 3 | 29 at 1.87 mpk | |
| 4 | 42 at 1.87 mpk | 71.9 |
| 5 | 124 at 8.75 mpk | |
| 6 | 45 at 8.75 mpk | |
| 7 | 20 at 8.75 mpk | 49.5 |
| 8 | 33 at 1.87 mpk | 27.3 |
| 9 | 123 at 8.75 mpk | |
| 10 | 75 at 8.75 mpk | |
| 11 | 29 at 1.87 mpk | |
| 12 | 45 at 8.75 mpk | 37.9 |
| 13 | 29 at 8.75 mpk | | mpk = milligrams per kilogram

What is claimed is:

1. A method of treating heart failure in mammals by administering an effective amount of the compound of the formula

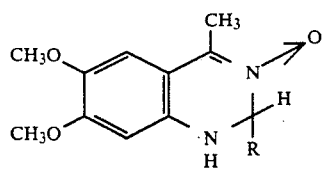

where

R is phenyl, substituted phenyl or heteroaryl; wherein said substituted phenyl is substituted with halogen, $C_1$-$C_6$ alkyl, $C_1$-$C_6$ alkoxy, methylenedioxy, nitro, benzyloxy, amino or substituted amino, and said heteroaryl is furyl, thienyl, pyrrolo, N-substituted pyrrolo, pyridyl or substituted heteroaryl; wherein said substituted amino is substituted with $C_1$-$C_6$ alkyl or $C_1$-$C_6$ dialkyl, said N-substituted pyrrolo is substituted with $C_1$-$C_6$ alkyl and said substituted heteroaryl is substituted with halogen, $C_1$-$C_6$ alkyl, $C_1$-$C_6$ alkoxy, methylenedioxy, nitro, benzyloxy, amino or substituted amino; wherein said substituted amino is substituted with $C_1$-$C_6$ alkyl or $C_1$-$C_6$ dialkyl.

2. A method of treating heart failure in mammals by administering an effective amount of the compound of the formula

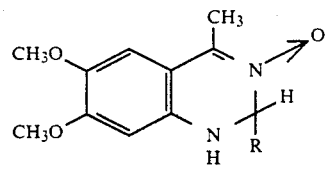

wherein R is phenyl, substituted phenyl, furyl, thienyl, pyrrolo, N-substituted pyrrolo or pyridyl.

3. A method of treating heart failure in mammals by administering an effective amount of 1,2-dihydro-2-phenyl-4-methyl-6,7-dimethoxyquinazoline-3-oxide.

4. A method of treating heart failure in mammals by administering an effective amount of the compound selected from the group consisting of 1,2-dihydro-2-(4-chlorophenyl)-4-methyl-6,7-dimethoxyquinazoline-3-oxide; 1,2-dihydro-2-(4-methoxyphenyl)-4-methyl-6,7-dimethoxyquinazoline-3-oxide; 1,2-dihydro-2-(4-tolyl)-4-methyl-6,7-dimethoxyquinazoline-3-oxide; 1,2-dihydro-2-(3,4-methylenedioxyphenyl)-4-methyl-6,7-dimethoxyquinazoline-3-oxide; 1,2-dihydro-2-(2,3-methylene-dioxyphenyl)-4-methyl-6,7-dimethoxyquinazoline-3-oxide; 1,2-dihydro-2-(3-benzyloxyphenyl)-4-methyl-6,7-dimethoxyquinazoline-3-oxide; 1,2-dihydro-2-pentafluorophenyl-4-methyl-6,7-dimethoxy-quinazoline-3-oxide; 1,2-dihydro-2-(2-furyl)-4-methyl-6,7-dimethoxyquinazoline-3-oxide; 1,2-dihydro-2-(2-thienyl)-4-methyl-6,7-dimethoxyquinazoline-3-oxide; 1,2-dihydro-2-(2-(N-methyl)pyrrolo)-4-methyl-6,7-dimethoxyquinazoline-3-oxide; and 1,2-dihydro-2-(2-pyridyl)-4-methyl-6,7-dimethoxyquinazoline-3-oxide and 1,2-dihydro-2-(4-pyridyl)-4-methyl-6,7-dimethoxyquinazoline-3-oxide.

* * * * *

UNITED STATES PATENT AND TRADEMARK OFFICE
CERTIFICATE OF CORRECTION

PATENT NO. : 5,030,635

DATED : July 9, 1991

INVENTOR(S) : Donald W. Combs et al.

It is certified that error appears in the above-identified patent and that said Letters Patent is hereby corrected as shown below:

In column 9, lines 20 and 21, "substituted amino is substituted with $C_1$-$C_6$ alkyl or $C_1$-$C_6$ dialkyl, said" should be deleted Signed and Sealed this Fifteenth Day of June, 1993

Attest:

MICHAEL K. KIRK

Attesting Officer     Acting Commissioner of Patents and Trademarks